United States Patent [19]

Torguet et al.

[11] 4,007,373

[45] Feb. 8, 1977

[54] RADIOGRAPHIC APPARATUS

[75] Inventors: Roger Torguet; Michel Frechede, both of Paris, France

[73] Assignee: Thomson-CSF, Paris, France

[22] Filed: Sept. 23, 1975

[21] Appl. No.: 616,010

[30] Foreign Application Priority Data

Sept. 27, 1974 France ............................ 74.32653

[52] U.S. Cl. ............................................. 250/355

[51] Int. Cl.$^2$ ...................... A61B 6/00; H05G 1/46

[58] Field of Search ............ 250/355, 205; 356/202

[56] References Cited

UNITED STATES PATENTS

| | | | |
|---|---|---|---|
| 2,723,350 | 11/1955 | Clapp | 250/355 |
| 3,542,479 | 11/1970 | Sibalis | 250/205 |

*Primary Examiner*—Alfred E. Smith
*Assistant Examiner*—T. N. Grigsby
*Attorney, Agent, or Firm*—Cushman, Darby & Cushman

[57] ABSTRACT

A radiographic apparatus for determining the absorption coefficient of bodies to be examined in which the radiation power is controlled by a negative feedback circuit, so as to be increased as a function of the absorption coefficient of the region under examination. Elements are provided for taking a predetermined fraction of the radiation, and for eliminating the variation of the power from the equation which gives the absorption coefficient.

6 Claims, 4 Drawing Figures

RADIOGRAPHIC APPARATUS

It is known within the field of radiography to utilise an X ray source emitting radiation which is directed on to a determinate portion of the body being studied, systems capable of picking up said radiation and translating into electrical signals being rigidly associated with said source.

In the known devices of this kind, the intensity of the X radiation is constant and is chosen to be sufficient to furnish information which can be used whatever the absorption coefficient of that part of the body which is being explored. However, it appears that the variations in this coefficient, are the information it is desired to obtain. To achieve these results, it is necessary to utilise a sufficient intensity to pick up usable signals when the region being examined has a lower absorbing power. This intensity could be superfluous, if the mean absorbing power were very much less.

The object of the present invention is to adjust this intensity in order to obtain the desired information, on the one hand without any information loss and on the other without adversely affecting the accuracy of examination.

The radiographic observation apparatus in accordance with the invention, comprises a radiation source, means for focussing the radiation and creating a beam in order to irradiate a determinate portion of the body to be examined, and transducers rigidly associated with said source, said transducers furnishing electrical signals and having, associated with them, elements designed to pick up and store the corresponding data. The apparatus is characterised essentially in that on the one hand first elements are provided in order to vary the intensity of the radiation beam so that said intensity is the higher the greater the overall absorbing power of the region through which it passes; on the other hand, second elements which make it possible to take account in the measurements which are made, of said variations in intensity.

The invention will be better understood from a consideration of the ensuing description and by reference to the attached drawings in which.

Figure 1:
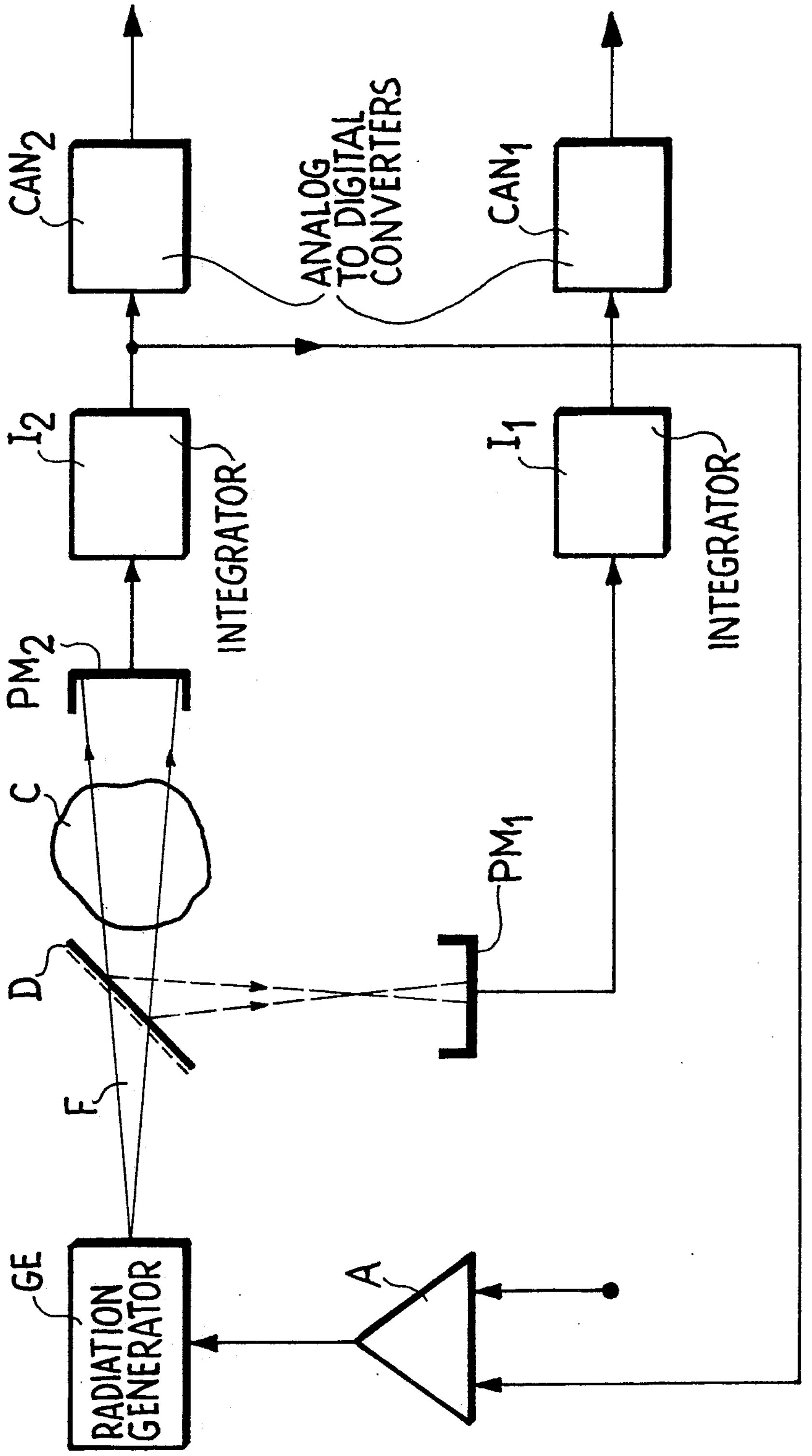
FIG. 1 is a block diagram of the device in accordance with the invention.

In FIG. 1, a radiation generator GE, more particularly an X or other penetrating ray generator, emits a thin particle beam F.

In the path of this beam there is arranged a diffuser D which has the property of passing a substantial proportion of the incident rays, the intensity of said portion being a fixed and determinate fraction of the incident intensity.

In order to provide a concrete example, if E is the emitted energy, the transmitted portion will be $K_2E$, where $K_2$ is a constant characteristic factor of the diffuser D.

The untransmitted portion of the intensity is scattered.

The system shown in FIG. 1 comprises two chains of identical elements, one receiving the radiation $K_2E$ and the other receiving a portion, of the scattered radiation, namely an energy $K_1E$, where $K_1$ is substantially less than $1 - K_2$.

The chain of elements receiving the scattered energy comprises a photo-detector-photo-multiplier unit $PM_1$ which transmits its output signal to an integrator $I_1$. The electrical output signal from the integrator is converted into digital data proportional to $E_1$, by an analogue-digital CAN 1.

The transmitted energy is utilised for radiological examination, passing through the element C which is to be studied, and a portion $K_2K_3E$ passes through said body, $K_3$ being the transmission coefficient of that portion of the body in question, in fact the coefficient which the device is intended to measure.

The second chain of elements is arranged downstream of said body, as it were, and comprises elements $PM_2$, $I_2$, $CAN_2$ identical respectively to $PM_1$, $I_1$, $CAN_1$.

An output of the integrator $I_2$ furnishes an electrical signal for example a voltage $V_2$, proportional to $K_2K_3E$. This voltage is applied to a first input of an operational amplifier A supplied at its second input with a reference fixed voltage $V_0$. The amplifier furnishes a voltage $V_D$ proportional to the difference $V_o - V_G$, the sign of which is positive if $V_o > V_D$ and negative if the contrary is the case. This voltage $V_D$ is applied to a control input of the radiation source GE. The voltage has the effect of controlling the intensity of the emitted radiation, without, however, modifying the energy spectrum thereof.

The operation of the system is as follows:

The chain $PM_1$-$I_1$-$CAN_1$ furnishes a number proportional to $K_1E$, where $K_1$ is constant.

The chain $PM_2$-$I_1$-$CAN_2$ furnishes a number proportional to $K_3K_2E$, where $K_3$ is unknown but $K_2$ is constant, the ratio $K_2/K_1$ being a characteristic parameter of the diffuser D. If E were constant, the number $K_3K_2E$ would readily give $K_3$. However, it is found that the body under examination is not uniform so that $K_3$ varies and in certain cases in order to obtain any results, it is necessary to use a substantial energy E, this energy being superfluous in other cases.

The negative feedback loop $I_2$ - A has the effect of varying E and of adjusting it to an appropriate value. E is therefore not constant and is unknown. The two converters which give numbers corresponding to $K_2K_3E$ and $K_1E$ respectively, make it possible to eliminate E from the equation for $K_3$.

Figure 2:
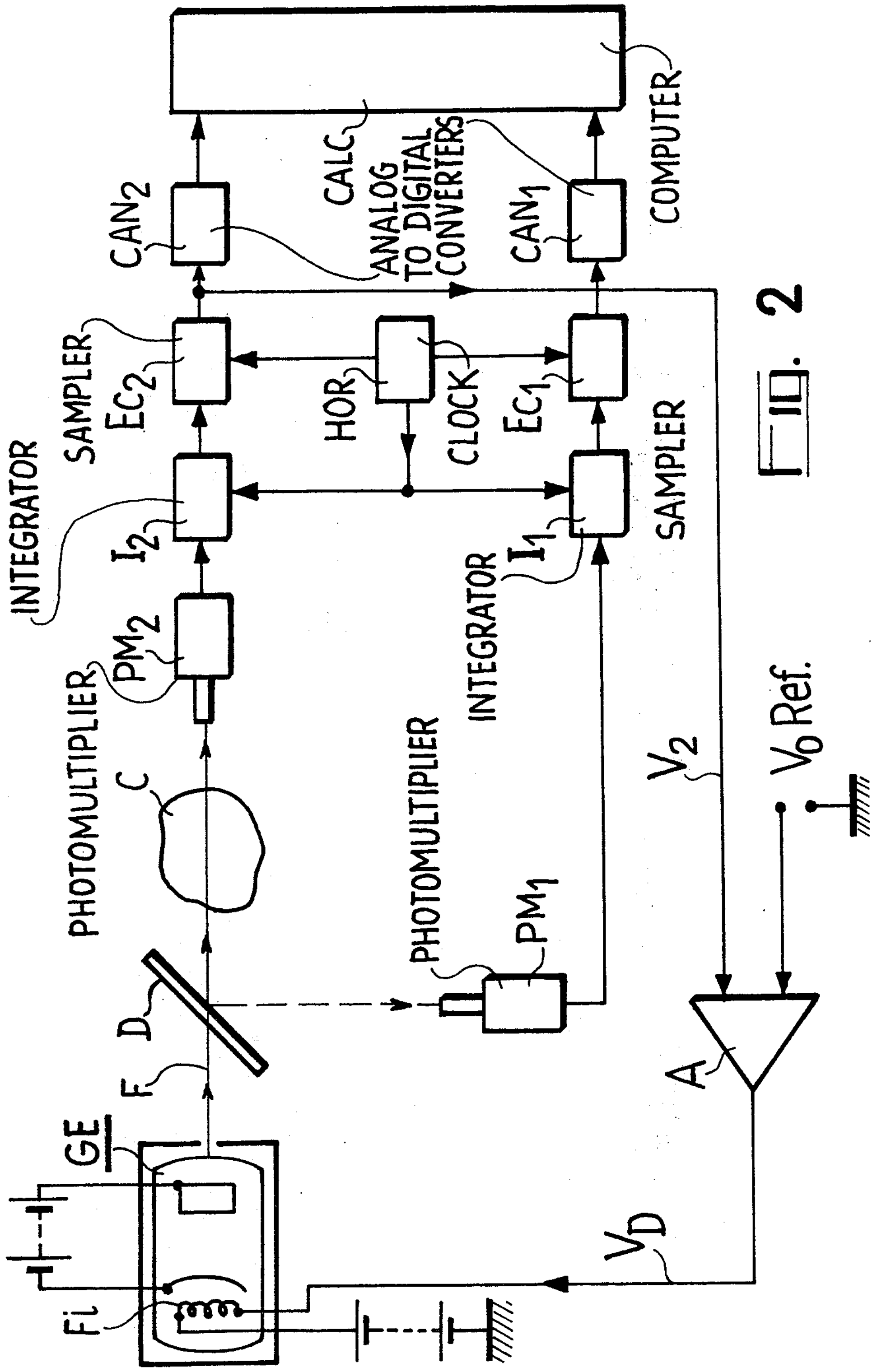
FIG. 2 is an embodiment of the device shown in FIG. 1.

FIG. 2 illustrates a non-limitative embodiment of the device shown in FIG. 1. Similar references designate similar elements.

The generator GE is of conventional design. The control device acts upon the filament *Fi*; the cathode emits an electron beam which is a monotonous function of the current flowing through the filament, and, finally, the X rays emitted by the anode AN have an intensity proportional to that of the incident electrons.

The two chains comprise the same elements. The index 1 is assigned to those of the first chain, the index 2 to those of the second.

These two chains comprise respectively photodetector-photomultiplier units $PM_1$ and $PM_2$ at the outputs of which integrators $I_1$ and $I_2$ are arranged controlled by a common time base HOR and emitting a pulsetrain of fixed recurrence frequency.

These two integrators supply their output voltages respectively to two samplers $EC_1$ and $EC_2$. These samplers are connected respectively to two analogue-digital converters $CAN_1$ and $CAN_2$, which transmit their digital information to a computer CALC, the latter, from said data, computing the opacity of the regions traversed by the radiation. The output voltage from $EC_2$ is the first element in the negative feedback loop described in FIG. 1.

Figure 3:
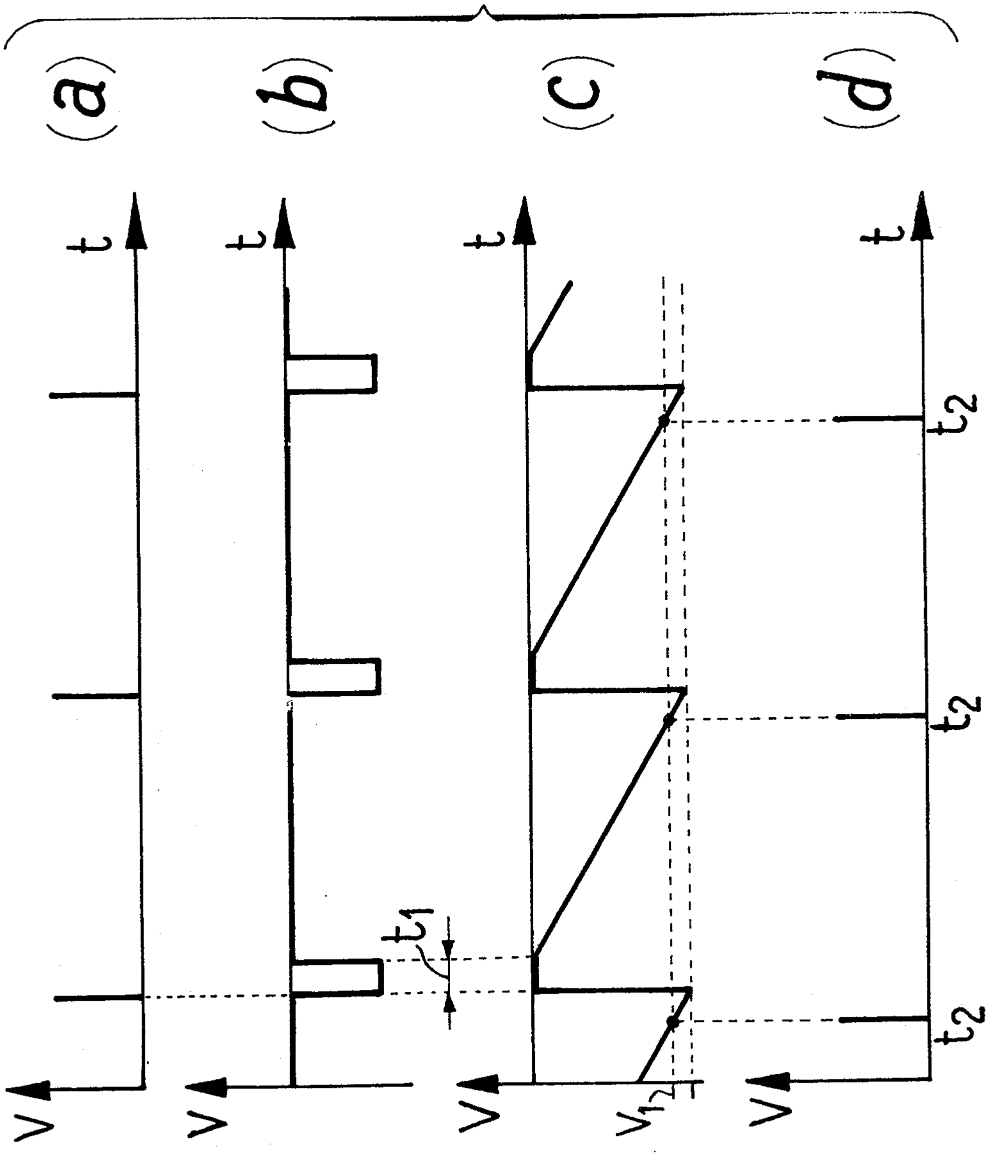
FIG. 3 is a set of explanatory graphs.

The operation of the system, will be understood from a consideration of the graphs shown in FIG. 3. These represent the voltages at various points in the device, as a function of time.

The graph (a) represents pulses emitted by the time base or clock HOR.

The graph (b) illustrates pulses of duration $t_1$ and of the same recurrence frequency, which make it possible to reset the two integrators to zero.

At the end of each reset pulse, each integrator furnishes a saw-tooth shaped voltage with a slope which is a function of the intensity of the radiations received by the two transducers $PM_1$ and $PM_2$.

In the example illustrated, the slope is negative but it goes without saying that it depends upon the arrangement of the integrator element.

The clock, at the end of a given time $t_2$ which is less than the periodicity of the pulses, controls the samplers which are supplied with the voltage V furnished by the integrator at the time $t_2$, graph (d). The voltages $V_1$ and $V_2$ furnished respectively by the integrators $I_1$ and $I_2$ are characteristic of the coefficients $K_2K_3E$ on the one hand and $K_1E$ on the other.

Only the curve corresponding to integrator I is shown. They are stored by the sampler which transmits them to the converters $CAN_1$ and $CAN_2$.

With each reset pulse, the integrator voltage is reset to zero.

Figure 4:
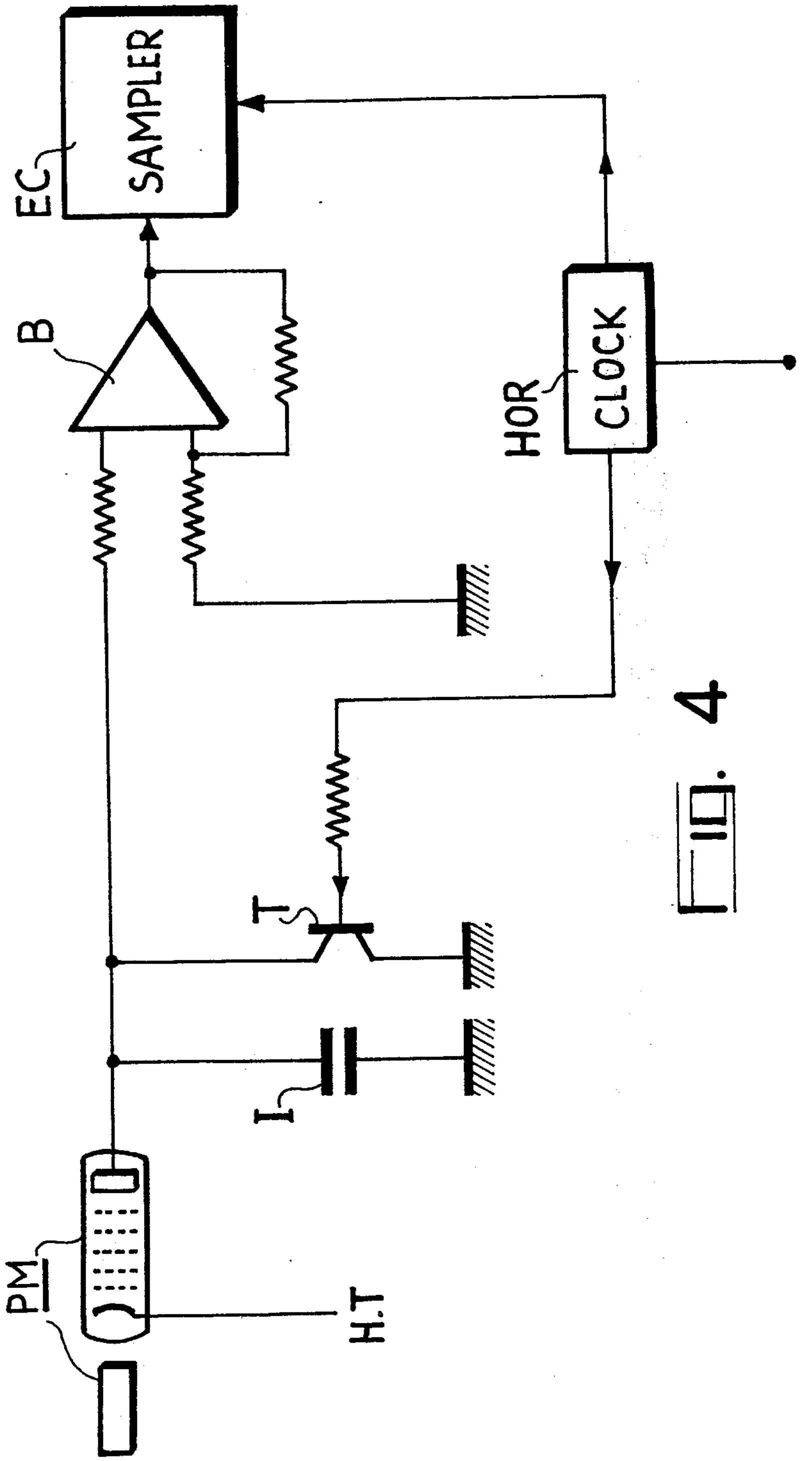
FIG. 4 illustrates an embodiment of a detail of the device shown in FIG. 2.

FIG. 4 is a non-limitative example of the detector circuits.

The integrator 1 is a capacitor one of whose terminals is earthed. It is followed by a constant-gain amplifier B connected to the sampler. The reset device is a simple transistor T, normally blocked, but driven conductive by the reset pulses.

In an example which has been built, the following were the parameters:

X ray tube acceleration voltage 100 KV;
photomultiplier supply voltage 1500 V;
capacitance of the integrating capacitor $C = 680$ pF;
hum voltage of the detection system, at the sampler, in the absence of any radiation emission, $Vz = 2$ mV.
$V_D$ voltage level at the input of the detecting device.

Several trials have been carried out:

1st trial

Subject analysed 25 cm of water + 7 mm thick bone;
Current intensity I of X ray emission tube $RX = 3.5$ mA for $VD/Vz = 2500$.

2nd trial

Subject analysed 25 cm of water + 7 mm thick bone + 0.5 dural filter;
Current intensity I of X ray emission tube $RX = 3.6$ mA for $VD/Vz = 2500$.

3rd trial

Subject analysed 25 cm of paraffin + 1 cm thick bone + 0.5 dural filter;
Current intensity I of X ray emission tube $RX = 2.6$ mA for $VD/Vz = 2500$.

In determining the measurement conditions, it will be noted that the ratio $VD/Vz = 2500$ has been chosen as a precaution. The power required for emission of the radiation was 360 watts maximum, very much less than the emission required in the prior art to give a detectable variation in opacity of the same order of magnitude. In the case where a minimum relative variation in opacity to be detected, would be 1/1000, the ratio $V_D/Vz$ would be $V_D/Vz = 1000$, the power required for the emission of the corresponding radiation would be reduced in the same proportion or, for the same power, the integration time and therefore the measurement time would be reduced in said same ratio, which comes down in both cases to a reduction in the dose absorbed by the subject during a series of measurements.

What we claim is:

1. A radiographic observation apparatus comprising:
an X-ray beam generating source for producing an X-ray beam for irradiating a predetermined portion of a body, and having an input for varying the energy of said beam as a function of an applied electrical signal;
first electrical transducer means for receiving said beam after passage through said body and producing at an output an electrical signal which varies as a function thereof;
means disposed over the beam trajectory for receiving said beam prior to passage through said body and for scattering a predetermined fraction of said beam energy;
second electrical transducer means for receiving said scattered energy fraction and producing at an output an electrical signal which varies as a function thereof;
means defining a feedback loop connected between said first transducer means output and said source input for applying said signal at the output of said first transducer means to said input;
means for transducing into first and second sets of digital data the electrical signals respectively produced by said first and second transducer means, said first set of data indicating the absorption coefficient of said body, and of said radiation energy and said second set of data indicating the radiated energy.

2. An apparatus as claimed in claim 1, wherein said scattering means comprises a diffuser.

3. An apparatus as claimed in claim 2, wherein said feedback loop defining means comprises an operational amplifier, having a first input receiving a reference voltage, and a second input connected to said first transducer means output.

4. An apparatus as claimed in claim 2, wherein said first and second transducer means each comprise, respectively, a serially connected photodetector, photomultiplier, and integrator, the integrator of said first transducer means having an output connected to the second input of said operational amplifier, and wherein each said transducing means includes an analog to digital converter connected respectively to an integrator, and data processing means connected to said analog to digital converters for receiving said sets of data for computing from said first and second data the absorption coefficient of said body.

5. An apparatus as claimed in claim 4, further comprising first and second sampler circuits, respectively connected between the integrators and analog to digital converters of said first and second transducing and transducer means, respectively, and a clock circuit having a first output connected to said sampler circuits for controlling said sampler circuits and a second output connected to said integrators for resetting said integrators to zero.

6. An apparatus as in claim 5, wherein each said integrator includes a capacitor and said clock circuit includes a transistor connected to said capacitor for controlling charging and discharging of said capacitor.

* * * * *